(12) United States Patent
Kozasa et al.

(10) Patent No.: US 6,544,440 B1
(45) Date of Patent: Apr. 8, 2003

(54) COATED BIS(2-PYRIDINETHIOL-1-OXIDE) COPPER SALT

(75) Inventors: Yasuhiro Kozasa, Fukuoka (JP); Yoshifumi Shibuya, Osaka (JP); Toshio Morishita, Osaka (JP); Yasuhiro Hidaka, Sakai (JP); Hiroyuki Akashi, Fukuoka (JP)

(73) Assignee: API Corporation, Osaka (JP)

( * ) Notice: Subject to any disclaimer, the term of this patent is extended or adjusted under 35 U.S.C. 154(b) by 0 days.

(21) Appl. No.: 09/700,648

(22) PCT Filed: Mar. 17, 2000

(86) PCT No.: PCT/JP00/01638
§ 371 (c)(1),
(2), (4) Date: Nov. 17, 2000

(87) PCT Pub. No.: WO00/54589
PCT Pub. Date: Sep. 21, 2000

(30) Foreign Application Priority Data

Mar. 17, 1999 (JP) ............................. 11-072727
Apr. 20, 1999 (JP) ............................. 11-112957
Apr. 20, 1999 (JP) ............................. 11-112958

(51) Int. Cl.[7] .................. C23F 11/01; C09K 15/20; C09D 5/16
(52) U.S. Cl. ................ 252/389.53; 252/400.53; 252/82; 252/182.33; 106/16; 106/17; 106/18.33
(58) Field of Search ................ 106/16, 17, 18, 106/18.33; 252/389.53, 400.53, 182.33, 82

(56) References Cited

U.S. PATENT DOCUMENTS

| 5,057,153 A | * | 10/1991 | Ruggiero ................ 106/18.33 |
| 5,185,033 A | * | 2/1993 | Hani et al. ............... 106/18.33 |
| 5,238,490 A | | 8/1993 | Farmer, Jr. et al. ...... 106/18.33 |
| 5,252,123 A | * | 10/1993 | Hani et al. ............... 106/18.33 |
| 5,643,593 A | | 7/1997 | Fersch et al. ............. 424/419 |
| 5,795,374 A | * | 8/1998 | Itoh et al. ..................... 106/16 |

FOREIGN PATENT DOCUMENTS

| AU | 16557/95 | 11/1995 |
| EP | 132301 | 1/1985 |
| EP | 0 651 034 | 5/1995 |
| JP | 48-75730 | 10/1973 |
| JP | 50-53538 | 5/1975 |
| JP | 53-27630 | 3/1978 |
| JP | 54-15939 | 2/1979 |
| JP | 54-78733 | 6/1979 |
| JP | 55-36221 | 3/1980 |
| JP | 56-59701 | 5/1981 |
| JP | 57-159701 | 10/1982 |
| JP | 3-120201 | 5/1991 |
| JP | 6-100405 | 4/1994 |
| JP | 8-269388 | 10/1996 |
| JP | 9-273075 | 10/1997 |
| JP | 10-298455 | 11/1998 |
| JP | 11-29402 | 2/1999 |
| JP | 2000-1410 A | 1/2000 |
| JP | 2000-26649 | 1/2000 |
| JP | 2000-72989 | 3/2000 |

\* cited by examiner

Primary Examiner—Joseph D. Anthony
(74) Attorney, Agent, or Firm—Wenderoth, Lind & Ponack, L.L.P.

(57) ABSTRACT

The present invention provides a bis(2-pyridinethiol-1-oxide) copper salt coated with one or more compounds selected from glycerin, dialkyl phthalate, lubricating oil, acrylic resin, rosin, fatty acid amide, dialkyl polysulfide, polybutene, paraffin and petrolatum. The coated copper salt does not scatter, so that it is easy to handle, and is superior in safety and workability. In addition, the copper salt does not suffer from any adverse influence on the inherent storage stability or antifouling effect by being coated. Therefore, a coating for the bottom of a ship having a superior antifouling effect and storage stability can be obtained.

2 Claims, No Drawings

COATED BIS(2-PYRIDINETHIOL-1-OXIDE) COPPER SALT

This application is a 371 of PCT/JP00/01638 filed Mar. 17, 2000.

TECHNICAL FIELD

The present invention relates to a composition containing an antifouling active ingredient for a coating for the bottom of a ship, which is safe during handling (e.g., transport) and coating operation and which is superior in an antifouling effect.

BACKGROUND ART

A bis(2-pyridinethiol-1-oxide) copper salt is effective as an industrial biocide and has been drawing much attention in recent years as a substitute antifouling active ingredient for organic tin.

The salt is in the form of fine and stiff needle-like crystals and tends to scatter as powder dust. This compound does not cause much irritation to a worker's fingers or hands upon contact, but when it comes into contact with the mucous membrane of nose, eye, trachea, lung and the like, it causes strong irritation. Particularly, when it is inhaled into the lung in a large amount, more serious disorders may be caused by the stiff needle crystals. To prevent this, workers should be extremely cautious not to inhale the compound or to allow adhesion thereof to the eye, skin, or clothes. For this end, workers put on suitable protective equipments, such as a dust preventive mask, protective glasses, protective gloves, protective clothes and the like, during handling of this compound. In addition, a local exhaust system is installed so as not to contaminate the work environment with the powder dust. However, the above-mentioned countermeasures are not sufficient to completely prevent workers from being exposed to the scattered powder dust. What is worse, these countermeasures strikingly lower the work efficiency.

DISCLOSURE OF THE INVENTION

The present invention aims at solving these problems and provides a composition containing a bis(2-pyridinethiol-1-oxide) copper salt, which is an antifouling component of a coating for the bottom of a ship and which is free from an adverse influence on the effectiveness of the compound.

The present inventors have conducted intensive studies in an attempt to solve the above-mentioned problems of the conventional bis(2-pyridinethiol-1-oxide) copper salt, and arrived at the coated bis(2-pyridinethiol-1-oxide) copper salt of the present invention. That is, they have found that coating of the bis(2-pyridinethiol-1-oxide) copper salt with a specific coating agent suppresses scattering of the powder dust, which in turn improves safety of the worker and work performance, and that a coating for the bottom of a ship, which contains this coated bis(2-pyridinethiol-1-oxide) copper salt, shows a stable effect for a long time without an adverse influence on the antifouling effect and shows the same stability during a long-term storage, which resulted in the completion of the present invention.

Accordingly, the present invention provides the following.

[1]: A bis(2-pyridinethiol-1-oxide) copper salt coated with a coating agent containing one or more kinds of compounds selected from the group consisting of glycerin, dialkyl phthalate, lubricating oil, acrylic resin, rosin, fatty acid amide, dialkyl polysulfide, polybutene, paraffin and petrolatum.

[2]: The coated bis(2-pyridinethiol-1-oxide) copper salt of [1], wherein the glycerin, dialkyl phthalate, lubricating oil, acrylic resin, rosin, fatty acid amide, dialkyl polysulfide, polybutene, paraffin or petrolatum is contained in an amount of 1–40 parts by weight per 100 parts by weight of the bis(2-pyridinethiol-1-oxide) copper salt.

[3]: The coated bis(2-pyridinethiol-1-oxide) copper salt of [2], wherein the amount of the one or more kinds of compounds selected from the group consisting of glycerin, dialkyl phthalate, lubricating oil, acrylic resin, rosin, fatty acid amide, dialkyl polysulfide, polybutene, paraffin and petrolatum is 1–40 parts by weight in total per 100 parts by weight of the bis(2-pyridinethiol-1-oxide) copper salt.

[4]: The coated bis(2-pyridinethiol-1-oxide) copper salt of [1], wherein the bis(2-pyridinethiol-1-oxide) copper salt is coated with 1–40 parts by weight of glycerin per 100 parts by weight of the bis(2-pyridinethiol-1-oxide) copper salt.

[5]: The coated bis(2-pyridinethiol-1-oxide) copper salt of [1], wherein the bis(2-pyridinethiol-1-oxide) copper salt is coated with 1–40 parts by weight of dialkyl phthalate per 100 parts by weight of the bis(2-pyridinethiol-1-oxide) copper salt.

[6]: The coated bis(2-pyridinethiol-1-oxide) copper salt of [1], wherein the bis(2-pyridinethiol-1-oxide) copper salt is coated with 1–40 parts by weight of a lubricating oil per 100 parts by weight of the bis(2-pyridinethiol-1-oxide) copper salt.

[7]: The coated bis(2-pyridinethiol-1-oxide) copper salt of [1], wherein the bis(2-pyridinethiol-1-oxide) copper salt is coated with 1–40 parts by weight of an acrylic resin per 100 parts by weight of the bis(2-pyridinethiol-1-oxide) copper salt.

[8]: The coated bis(2-pyridinethiol-1-oxide) copper salt of [1], wherein the bis(2-pyridinethiol-1-oxide) copper salt is coated with 1–40 parts by weight of rosin per 100 parts by weight of the bis(2-pyridinethiol-1-oxide) copper salt.

[9]: The coated bis(2-pyridinethiol-1-oxide) copper salt of [1], wherein the bis(2-pyridinethiol-1-oxide) copper salt is coated with 1–40 parts by weight of fatty acid amide per 100 parts by weight of the bis(2-pyridinethiol-1-oxide) copper salt.

[10]: A composition containing the coated bis(2-pyridinethiol-1-oxide) copper salt of [1], wherein the bis(2-pyridinethiol-1-oxide) copper salt is coated with 1–40 parts by weight of dialkyl polysulfide per 100 parts by weight of the bis(2-pyridinethiol-1-oxide) copper salt.

[11]: The coated bis(2-pyridinethiol-1-oxide) copper salt of [1], wherein the bis(2-pyridinethiol-1-oxide) copper salt is coated with 1–40 parts by weight of polybutene per 100 parts by weight of the bis(2-pyridinethiol-1-oxide) copper salt.

[12]: The coated bis(2-pyridinethiol-1-oxide) copper salt of [1], wherein the bis(2-pyridinethiol-1-oxide) copper salt is coated with 1–40 parts by weight of paraffin per 100 parts by weight of the bis(2-pyridinethiol-1-oxide) copper salt.

[13]: The coated bis(2-pyridinethiol-1-oxide) copper salt of [1], wherein the bis(2-pyridinethiol-1-oxide) copper salt is coated with 1–40 parts by weight of petrolatum per 100 parts by weight of the bis(2-pyridinethiol-1-oxide) copper salt.

The bis(2-pyridinethiol-1-oxide) copper salt is known as a compound superior in antifouling property due to its biocidal effect and is used as an antifouling component of a coating for marine craft and the like, such as a coating for the bottom of a ship and the like. This copper salt is commercially available and can be produced by the method disclosed in, for example, U.S. Pat. No. 2,809,971.

The bis(2-pyridinethiol-1-oxide) copper salt is coated with a coating agent containing one or more kinds of the compounds selected from the group consisting of glycerin, dialkyl phthalate, lubricating oil, acrylic resin, rosin, fatty acid amide, dialkyl polysulfide, polybutene, paraffin and petrolatum.

Examples of glycerin include diglycerin, polyglycerin and the like, besides typically used glycerin. These may be used in admixture.

The alkyl moiety of dialkyl phthalate preferably has 1 to 18 carbon atoms. Examples thereof include diethyl phthalate, dibutyl phthalate, diheptyl phthalate, dioctyl phthalate and the like. These may be used in admixture.

Examples of lubricating oil include spindle oil, dynamo oil machine oil, engine oil, turbine oil, silicon oil and the like. These may be used in admixture. Other hardly volatile substances, such as higher alcohols (e.g., polyethylene glycol, stearyl alcohol and the like) and the like may be used concurrently.

Examples of acrylic resin include homopolymers and copolymers of acrylic esters such as methyl acrylate, ethyl acrylate, n-propyl acrylate, i-propyl acrylate, n-butyl acrylate, i-butyl acrylate, t-butyl acrylate, 2-ethylhexyl acrylate, lauryl acrylate, cetyl acrylate, stearyl acrylate, vinyl acrylate, benzyl acrylate, phenyl acrylate, isobornyl acrylate, cyclohexyl acrylate, glycidyl acrylate, 2-hydroxyethyl acrylate, 2-hydroxypropyl acrylate, 2-hydroxybutyl acrylate, 4-hydroxybutyl acrylate, glycerol acrylate, butylaminoethyl acrylate, dimethylaminoethyl acrylate, diethylaminoethyl acrylate, dimethylaminopropyl acrylate, dimethylaminobutyl acrylate, dibutylaminoethyl acrylate, 2-methoxyethyl acrylate, 2-ethoxyethyl acrylate, phenoxyethyl acrylate, 2-(2-ethylhexaoxy)ethyl acrylate, 1-methyl-2-methoxyethyl acrylate, 3-methoxybutyl acrylate, 3-methyl-3-methoxybutyl acrylate, o-methoxyphenyl acrylate, m-methoxyphenyl acrylate, p-methoxyphenyl acrylate, o-methoxyphenylethyl acrylate, m-methoxyphenylethyl acrylate, p-methoxyphenylethyl acrylate and the like; metal salts of acrylic acid such as zinc acrylate, zinc benzoate acrylate, zinc propionate acrylate, zinc octanoate acrylate, zinc barsatate acrylate, zinc stearate acrylate, zinc isostearate acrylate, zinc palmitate acrylate, zinc cresotinate acrylate, zinc α-naphthoate acrylate, zinc β-naphthoate acrylate, zinc monochloroacetate acrylate, zinc monofluoroacetate acrylate, zinc 2,4-dichlorophenoxyacetate acrylate, zinc 2,4,5-trichlorophenoxyacetate acrylate, zinc quinolinecarboxylate acrylate, zinc nitrobenzoate acrylate, zinc nitronaphthalenecarboxylate acrylate, zinc pulvinate acrylate, copper acrylate, copper benzoate acrylate, copper propionate acrylate, copper octanoate acrylate, copper barsatate acrylate, copper stearate acrylate, copper isostearate acrylate, copper palmitate acrylate, copper cresotinate acrylate, copper α-naphthoate acrylate, copper β-naphthoate acrylate, copper monochloroacetate acrylate, copper monofluoroacetate acrylate, copper 2,4-dichlorophenoxyacetate acrylate, copper 2,4,5-trichlorophenoxyacetate acrylate, copper quinolinecarboxylate acrylate, copper nitrobenzoate acrylate, copper nitronaphthalenecarboxylate acrylate, copper pulvinate acrylate, magnesium acrylate, magnesium benzoate acrylate, magnesium propionate acrylate, magnesium octanoate acrylate, magnesium barsatate acrylate, magnesium stearate acrylate, magnesium isostearate acrylate, magnesium palmitate acrylate, magnesium cresotinate acrylate, magnesium α-naphthoate acrylate, magnesium β-naphthoate acrylate, magnesium monochloroacetate acrylate, magnesium monofluoroacetate acrylate, magnesium 2,4-dichlorophenoxyacetate acrylate, magnesium 2,4,5-trichlorophenoxyacetate acrylate, magnesium quinolinecarboxylate acrylate, magnesium nitrobenzoate acrylate, magnesium nitronaphthalenecarboxylate acrylate, magnesium pulvinate acrylate, trimethylsilyl acrylate, triethylsilyl acrylate, tri-n-propylsilyl acrylate, tri-i-propylsilyl acrylate, tri-n-butylsilyl acrylate, tri-i-butylsilyl acrylate, triphenylsilyl acrylate, dimethylbutylsilyl acrylate, dimethylhexylsilyl acrylate, dimethyloctylsilyl acrylate, dimethylcyclohexylsilyl acrylate, dimethylphenylsilyl acrylate, methyldibutylsilyl acrylate, ethyldibutylsilyl acrylate, dibutylcyclohexylsilyl acrylate, dibutylphenylsilyl acrylate and the like; acrylic amides such as acrylamide, dimethylaminoethylacrylamide, dimethylaminopropylacrylamide and the like; methacrylic esters such as methyl methacrylate, ethyl methacrylate, n-propyl methacrylate, i-propyl methacrylate, n-butyl methacrylate, i-butyl methacrylate, t-butyl methacrylate, 2-ethylhexyl methacrylate, lauryl methacrylate, stearyl methacrylate, vinyl methacrylate, benzyl methacrylate, phenyl methacrylate, isobornyl methacrylate, cyclohexyl methacrylate, glycidyl methacrylate, 2-hydroxyethyl methacrylate, 2-hydroxypropyl methacrylate, 2-hydroxybutyl methacrylate, 4-hydroxybutyl methacrylate, glycerol methacrylate, butylaminoethyl methacrylate, dimethylaminoethyl methacrylate, diethylaminoethyl methacrylate, dimethylaminopropyl methacrylate, dimethylaminobutyl methacrylate, dibutylaminoethyl methacrylate, 2-methoxyethyl methacrylate, 2-ethoxyethyl methacrylate, phenoxyethyl methacrylate, 2-(2-ethylhexaoxy)ethyl methacrylate, 1-methyl-2-methoxyethyl methacrylate, 3-methoxybutyl methacrylate, 3-methyl-3-methoxybutyl methacrylate, o-methoxyphenyl methacrylate, m-methoxyphenyl methacrylate, p-methoxyphenyl methacrylate, o-methoxyphenylethyl methacrylate, m-methoxyphenylethyl methacrylate, p-methoxyphenylethyl methacrylate and the like; metal salts of methacrylic acid such as zinc methacrylate, zinc benzoate methacrylate, zinc propionate methacrylate, zinc octanoate methacrylate, zinc barsatate methacrylate, zinc stearate methacrylate, zinc isostearate methacrylate, zinc palmitate methacrylate, zinc cresotinate methacrylate, zinc α-naphthoate methacrylate, zinc β-naphthoate methacrylate, zinc monochaoroacetate methacrylate, zinc monofluoroacetate methacrylate, zinc 2,4-dichlorophenoxyacetate methacrylate, zinc 2,4,5-trichlorophenoxyacetate methacrylate, zinc quinolinecarboxylate methacrylate, zinc nitrobenzoate methacrylate, zinc nitronaphthalenecarboxylate methacrylate, zinc pulvinate methacrylate, copper methacrylate, copper benzoate methacrylate, copper propionate methacrylate, copper octanoate methacrylate, copper barsatate methacrylate, copper stearate methacrylate, copper isostearate methacrylate, copper palmitate methacrylate, copper cresotinate methacrylate, copper α-naphthoate methacrylate, copper β-naphthoate methacrylate, copper monochloroacetate methacrylate, copper monofluoroacetate methacrylate, copper 2,4-dichlorophenoxyacetate methacrylate, copper 2,4,5-trichlorophenoxyacetate methacrylate, copper quinolinecarboxylate methacrylate, copper nitrobenzoate methacrylate, copper nitronaphthalenecarboxylate methacrylate, copper pulvinate methacrylate, magnesium methacrylate, magnesium benzoate methacrylate, magnesium propionate methacrylate, magnesium octanoate methacrylate, magnesium barsatate methacrylate, magnesium stearate methacrylate, magnesium isostearate methacrylate, magnesium palmitate methacrylate, magnesium cresotinate methacrylate, magnesium α-naphthoate methacrylate, magnesium β-naphthoate methacrylate, magnesium monochloroacetate methacrylate, magnesium monofluoroacetate methacrylate, magnesium 2,4-dichlorophenoxyacetate methacrylate, magnesium 2,4,5-trichlorophenoxyacetate methacrylate, magnesium quinolinecarboxylate methacrylate, magnesium nitrobenzoate methacrylate, magnesium nitronaphthalenecarboxylate methacrylate, magnesium pulvinate methacrylate, trimethylsilyl methacrylate, triethylsilyl methacrylate, tri-n-propylsilyl methacrylate, tri-i-propylsilyl methacrylate, tri-n-butylsilyl methacrylate, tri-i-butylsilylacrylate, triphenylsilyl methacrylate, dimethylbutylsilyl methacrylate, dimethylhexylsilyl methacrylate, dimethyloctylsilyl methacrylate, dimethylcyclohexylsilyl methacrylate, dimethylphenylsilyl methacrylate, methyldibutylsilyl methacrylate, ethyldibutylsilyl methacrylate, dibutylcyclohexylsilyl methacrylate, dibutylphenylsilyl methacrylate and the like; methacrylic amides such as methacrylamide, dimethylaminoethylmethacrylamide, dimethylaminopropylmethacrylamide and the like; cyanoacrylic esters, acrolein, coumarone, indene and the like. These may be used in admixture.

Of these, a copolymer (glass transition temperature: −20° C. to 50° C.) of alkyl acrylate and alkyl methacrylate, and a self-polishing resin wherein a part of the carboxylic acid moiety of acrylic acid and methacrylic acid has been replaced with a divalent heavy metal salt (e.g., copper, zinc and the like) or —Si(R)$_3$ wherein R is alkyl having 1 to 18 carbon atoms, such as methyl, ethyl and the like, or ethoxy chain having 2 to 12 carbon atoms, and the like are preferable.

Examples of rosin include wood rosin, gum rosin, tall oil rosin and the like. Of these, wood rosin is preferable. These ay be used in admixture.

Examples of preferable fatty acid amide compound include amide compound of fatty acid having 11 or more carbon atoms, such as stearamide, palmitamide, methylenebisstearamide, ethylenebisstearamide, amide wax, polyamide wax and the like. These may be used in admixture.

As the dialkyl polysulfide, a compound of the formula (1)

$$R^1—(S)n—R^1 \tag{1}$$

wherein each $R^1$ is alkyl having 1 to 20 carbon atoms and n is an integer of 2 to 10, is preferable.

Preferable $R^1$ is, for example, ethyl, propyl, t-butyl, t-amyl, t-octyl, t-nonyl, t-dodecyl or nonadecyl.

Preferable dialkyl polysulfide of the formula (1) is, for example, diethyl pentasulfide, dipropyl tetrasulfide, di-t-butyl disulfide, di-t-octyl pentasulfide, di-t-nonyl pentasulfide, di-t-dodecyl pentasulfide, dinonadecyl tetrasulfide and the like. These may be used in admixture.

Dialkyl polysulfide can be used in admixture.

Examples of preferable polybutene include polybutene having an average molecular weight (Mn) of 200–1000, such as LV-5, LV-10, LV-25, LV-50, LV-100, HV-15, HV-35, HV-50, HV-100 and the like, all manufactured by NIPPON PETROCHEMICALS CO., LTD. These may be used in admixture.

Examples of paraffin include liquid paraffin, paraffin wax, paraffin chloride and the like. These may be used in admixture.

Examples of petrolatum include white petrolatum, yellow petrolatum and the like. These may be used in admixture.

For easy handling, acrylic resin and rosin are preferably dissolved in an organic solvent to give a solution and fatty acid amide is preferably wetted with an organic solvent to give a paste, both before use.

Examples of organic solvent include aromatic organic solvent and aliphatic organic solvent. Particularly, xylene, solvent naphtha, kerosene and alcohols are preferable. Of these, xylene is most preferable.

The contents of the above-mentioned active ingredients in a coating agent are appropriately determined. Each active ingredient to be used, such as glycerin, dialkyl phthalate, lubricating oil, acrylic resin, rosin, fatty acid amide, dialkyl polysulfide, polybutene, paraffin and petrolatum, is preferably contained in an amount of 1–40 parts by weight per 100 parts by weight of bis(2-pyridinethiol-1-oxide) copper salt.

Alternatively, the total amount of the active ingredients in the coating agent may be 1–40 parts by weight per 100 parts by weight of bis(2-pyridinethiol-1-oxide) copper salt.

When the amount of the above-mentioned active ingredient is within the above-mentioned range, bis(2-pyridinethiol-1-oxide) copper salt does not scatter and exerts no adverse influence on the property of the coating composition thus prepared.

When the active ingredient of the coating agent to be used is glycerin, dialkyl phthalate or lubricating oil, the amount thereof is preferably 1–10 parts by weight per 100 parts by weight of bis(2-pyridinethiol-1-oxide) copper salt. When plural ingredients are used, the total amount thereof is preferably 1–20 parts by weight per 100 parts by weight of bis(2-pyridinethiol-1-oxide) copper salt.

When the active ingredient of the coating agent to be used is acrylic resin, rosin or fatty acid amide, it is preferably prepared into a solution or paste before use, as mentioned above. When an acrylic resin is used, an organic solvent solution containing the acrylic resin in a proportion of 30–50 wt % is preferably used in a proportion of 5–40 parts by weight per 100 parts by weight of bis(2-pyridinethiol-1-oxide) copper salt. When rosin is used, an organic solvent solution containing the rosin in a proportion of 50–80 wt % is preferably used in a proportion of 5–40 parts by weight per 100 parts by weight of the above copper salt. When fatty acid amide is used, a paste containing the fatty acid amide in a proportion of 10–40 wt %, particularly preferably 10–30 wt %, is preferably used in a proportion of 5–40 parts by weight per 100 parts by weight of the above copper salt. The content thereof when two or three kinds of these coating agents are used is preferably 5–40 parts by weight of the total of the above-mentioned content acrylic resin solution, rosin solution and paste of fatty acid amide, per 100 parts by weight of bis(2-pyridinethiol-1-oxide) copper salt.

When the active ingredient of the coating agent to be used is dialkyl polysulfide, polybutene, paraffin or petrolatum, the amount to be used thereof is preferably 5–40 parts by weight per 100 parts by weight of bis(2-pyridinethiol-1-oxide) copper salt. When plural members are to be used, the total amount thereof is preferably 5–40 parts by weight per 100 parts by weight of bis(2-pyridinethiol-1-oxide) copper salt.

The coated bis(2-pyridinethiol-1-oxide) copper salt of the present invention can be obtained easily by mixing and kneading the predetermined amounts of bis(2-pyridinethiol-1-oxide) copper salt and a coating agent in various high speed mixers and kneaders. Examples of high speed mixer include mixers marketed with trademarks "HI-BLENDER", "ROLLER-MIXER", "HI-SPEEDER", "HI-SLUDGER", "PUG-MIXER" and the like, manufactured by PACIFIC MACHINERY AND ENGINEERING Co., Ltd. A method comprising dissolving a coating agent in an organic solvent, such as methanol, hexane and xylene, and mixing and kneading with bis(2-pyridinethiol-1-oxide) copper salt while evaporating the solvent under reduced pressure, or other methods can be used.

In the present specification, by "coating" is meant covering the entire surface of bis(2-pyridinethiol-1-oxide) copper salt with a coating agent, as well as partial attachment of the coating agent onto the surface of the copper salt, as long as the copper salt does not scatter as powder dust.

The coated bis(2-pyridinethiol-1-oxide) copper salt of the present invention is added to a coating for craft, such as a coating for the bottom of a ship and the like, a coating to be applied to underwater structures such as harbor facilities, buoy, undersea base, conduits of power plant, aquaculture net and the like, and the like.

EXAMPLES

The present invention is explained in detail in the following by referring to Examples. The present invention is not limited by these examples.

Example 1

Glycerin (5 parts by weight), di-n-butyl phthalate (5 parts by weight) and turbine oil (5 parts by weight) were added per 100 parts by weight of bis(2-pyridinethiol-1-oxide) copper salt, and the mixture was stirred in a Henschel mixer for 1 hr to give a bis(2-pyridinethiol-1-oxide) copper salt coated with the compound.

Examples 2–20

In the same manner as in Example 1, bis(2-pyridinethiol-1-oxide) copper salts coated with the compound having the antifouling effect explained in the specification was obtained. They are shown together in Table 1.

oxide) copper salt was added as an antifouling component, and subjected to the test.

TABLE 2

Composition of ship bottom coatings 1–20

| Ingredient | parts by weight |
|---|---|
| Antifouling component (Example 1–20) | 3.5 |
| Cuprous oxide | 20 |
| Iron oxide red | 8 |
| Talc | 4.5 |
| Resin | 10 |
| Rosin xylene solution | 25 |
| Amide wax | 2 |
| Xylene | 27 |
| | 100 |

The rosin xylene solution in Table 2 is a solution having a rosin component of 60 wt % and a xylene component of 40 wt %, the amide wax is a paste composition containing a fatty acid amide component (20 parts by weight %) and xylene (80 wt %), and the resin is a solution having a vinyl chloride-isobutyl vinyl ether copolymer component of 50 wt % and a xylene component of 50 wt %.

The coated bis(2-pyridinethiol-1-oxide) copper salts obtained in Examples 1–20 showed markedly improved workability, caused no irritation by inhalation, irritation to the skin or irritation to the mucous membrane, and were free of scattering. It was also found that the coated substance easily eluted out in the coating to again form a bis(2-pyridinethiol-1-oxide) copper salt.

The coating of Comparative Example using an uncoated bis(2-pyridinethiol-1-oxide) copper salt showed intensive

TABLE 1

| | Coating agent (parts by weight) Example | | | | | | | | | | | | | | | | | | |
|---|---|---|---|---|---|---|---|---|---|---|---|---|---|---|---|---|---|---|---|
| Coating agent | 2 | 3 | 4 | 5 | 6 | 7 | 8 | 9 | 10 | 11 | 12 | 13 | 14 | 15 | 16 | 17 | 18 | 19 | 20 |
| glycerine | | | 10 | 10 | | | | | | 20 | | | | | | | | | |
| di-n-butyl phthalate | | | 10 | | | | | | | | 20 | | | | | | | | |
| turbine oil | | | | 10 | | | | | | | | 20 | | | | | | | |
| *1 acrylic resin | 5 | | | | 10 | 10 | | | | | | | 20 | | | | | | |
| *2 rosin | 5 | | | | | 10 | | | | | | | | 20 | | | | | |
| *3 fatty acid amide | 5 | | | | | | 10 | | | | | | | | 20 | | | | |
| *4 dialkyl polysulfide | | 5 | | | | | 10 | 10 | 10 | | | | | | | 20 | | | |
| *5 polybutene | | 5 | | | | | 10 | | | | | | | | | | 20 | | |
| *6 paraffin | | 5 | | | | | | 10 | | | | | | | | | | 20 | |
| *7 petrolatum | | 5 | | | | | | | 10 | | | | | | | | | | 20 |

*1 Acrylic resin made from n-butylacrylate and methyl methacrylate, having a glass transition temperature of 0° C. (solution containing acrylic resin component 40 wt % and xylene 60 wt %).
*2 Solution containing rosin component 60 wt % and xylene 40 wt %.
*3 Paste composition containing fatty acid amide component 20 wt % and xylene 80 wt %.
*4 di-t-nonyl polysulfide
*5 LV-50 (product name, NIPPON PETROCHEMICALS CO., LTD.)
*6 Liquid paraffin
*7 Yellow petrolatum The coated bis(2-pyridinethiol-1-oxide) copper salts obtained in Examples 1–20 caused no occurrence of powder dust, unlike bis(2-pyridinethiol-1-oxide) copper salt needle crystals.

Using the coated bis(2-pyridinethiol-1-oxide) copper salts obtained in Examples 1–20 as the antifouling component, coatings for the bottom of ship were prepared according to the compositions shown in Table 2. As a Comparative Example, a coating was prepared in the same manner as in the examples except that an uncoated bis(2-pyridinethiol-1- scattering of powder dust during the preparation, as compared to the coatings of Examples of the present invention containing a coated copper salt, and caused irritation by inhalation, irritation to the skin and irritation to the mucous membrane. Due to the poor handling property, the workability was markedly impaired.

Stability Test

The coatings containing the coated bis(2-pyridinethiol-1-oxide) copper salts of Examples 1–20, which are for the bottom of ship, were placed in a pressure glass bottle and stood in a thermostat at 50° C. to perform accelerated deterioration test. The coatings were taken out after a predetermined number of days and the viscosity at 25° C. was measured by a Stomer viscometer. The results are shown in Table 3.

TABLE 3

| Ship bottom coating | Viscosity (K.U.) Stored at 50° C. | | | |
|---|---|---|---|---|
| | Immediately after storage | 1 week later | 2 weeks later | 4 weeks later |
| Example 1 | 80 | 80 | 88 | 88 |
| Example 2 | 78 | 79 | 79 | 79 |
| Example 3 | 83 | 83 | 83 | 84 |
| Example 4 | 83 | 89 | 91 | 91 |
| Example 5 | 82 | 87 | 89 | 89 |
| Example 6 | 84 | 86 | 87 | 87 |
| Example 7 | 80 | 81 | 81 | 81 |
| Example 8 | 82 | 84 | 85 | 86 |
| Example 9 | 79 | 79 | 83 | 85 |
| Example 10 | 81 | 83 | 83 | 84 |
| Example 11 | 82 | 82 | 85 | 85 |
| Example 12 | 81 | 83 | 85 | 85 |
| Example 13 | 85 | 87 | 87 | 89 |
| Example 14 | 81 | 84 | 86 | 86 |
| Example 15 | 80 | 85 | 85 | 87 |
| Example 16 | 83 | 84 | 86 | 86 |
| Example 17 | 79 | 80 | 81 | 81 |
| Example 18 | 82 | 87 | 88 | 88 |
| Example 19 | 77 | 80 | 80 | 81 |
| Example 20 | 80 | 82 | 84 | 84 |
| Comparative Example | 84 | 89 | 91 | 91 |

As is evident from Table 3, the coatings containing the coated bis(2-pyridinethiol-1-oxide) copper salts of Examples 1–20, which are for the bottom of ship, could be stored safely for a long period of time.

Effectiveness Test

The coatings of Examples 1–20, which are for the bottom of ship, were applied twice onto a steel plate previously coated with an antirust coating. The plate was immersed at about 1.5 meter underwater in the sea in the Tanabe bay in Wakayama-ken to observe adhesion of marine adhesion organisms. The area where the marine adhesion organisms adhered to was measured, the results of which are summarized in Table 4. The area of the steel plate where the marine adhesion organisms adhered to was shown in percentage, wherein adhesion of the marine adhesion organisms to the entirety of the steel plate was taken as 100, and the absence of adhesion of the marine adhesion organisms was taken as 0.

TABLE 4

Sea immersion test results (organisms adhesion area %)

| | Organisms adhesion area % | | | |
|---|---|---|---|---|
| | 3 months | 6 months | 9 months | 12 months |
| Example 1 | 0 | 0 | 0 | 0 |
| Example 2 | 0 | 0 | 0 | 0 |
| Example 3 | 0 | 0 | 0 | 5 |
| Example 4 | 0 | 0 | 0 | 0 |
| Example 5 | 0 | 0 | 0 | 5 |
| Example 6 | 0 | 0 | 0 | 5 |
| Example 7 | 0 | 0 | 0 | 0 |
| Example 8 | 0 | 0 | 0 | 5 |
| Example 9 | 0 | 0 | 0 | 0 |
| Example 10 | 0 | 0 | 0 | 0 |
| Example 11 | 0 | 0 | 0 | 0 |
| Example 12 | 0 | 0 | 0 | 0 |
| Example 13 | 0 | 0 | 0 | 0 |
| Example 14 | 0 | 0 | 0 | 0 |
| Example 15 | 0 | 0 | 0 | 5 |
| Example 16 | 0 | 0 | 0 | 0 |
| Example 17 | 0 | 0 | 0 | 0 |
| Example 18 | 0 | 0 | 0 | 0 |
| Example 19 | 0 | 0 | 0 | 0 |
| Example 20 | 0 | 0 | 0 | 0 |
| Comparative Example | 0 | 0 | 0 | 0 |
| untreated | 95 | 100 | 100 | 100 |

As is evident from Table 4, the coatings containing the antifouling components of Examples 1–20, which are for the bottom of ship, showed an antifouling effect over an extended period of time. It was also found that the effect was not inhibited at all by the coating with the compound of the present invention.

Example 21

Glycerin (3 parts by weight), di-n-butyl phthalate (3 parts by weight) and turbine oil (3 parts by weight) were added per 100 parts by weight of bis(2-pyridinethiol-1-oxide) copper salt, and the mixture was stirred in a Henschel mixer to give a bis(2-pyridinethiol-1-oxide) copper salt composition coated with the compound.

Example 22

Glycerin (1 part by weight), di-n-butyl phthalate (2 parts by weight) and turbine oil (2 parts by weight) were added per 100 parts by weight of bis(2-pyridinethiol-1-oxide) copper salt, and the mixture was stirred in a kneader for 1 hr to give a bis(2-pyridinethiol-1-oxide) copper salt coated with the compound.

Example 23

In the same manner as in Example 1 except that glycerin (5 parts by weight) was added as a coating agent, bis(2-pyridinethiol-1-oxide) copper salt coated with the compound was obtained.

Example 24

In the same manner as in Example 1 except that di-n-butyl phthalate (5 parts by weight) was added as a coating agent, bis(2-pyridinethiol-1-oxide) copper salt coated with the compound was obtained.

Example 25

In the same manner as in Example 1 except that turbine oil (5 parts by weight) was added as a coating agent, bis(2-pyridinethiol-1-oxide) copper salt coated with the compound was obtained.

Example 26

In the same manner as in Example 1 except that glycerin (5 parts by weight) and di-n-butyl phthalate (0.5 part by weight) were added as a coating agent, bis(2-pyridinethiol-1-oxide) copper salt coated with the compound was obtained.

Example 27

In the same manner as in Example 1 except that glycerin (5 parts by weight) and turbine oil (5 parts by weight) were added as a coating agent, bis(2-pyridinethiol-1-oxide) copper salt coated with the compound was obtained.

Example 28

Dialkyl polysulfide (5 parts by weight), polybutene (5 parts by weight) and petrolatum (5 parts by weight) were added per 100 parts by weight of bis(2-pyridinethiol-1-oxide) copper salt, and the mixture was stirred in a Henschel mixer for 1 hr to give a bis(2-pyridinethiol-1-oxide) copper salt coated with the compound.

The coated bis(2-pyridinethiol-1-oxide) copper salts obtained in Examples 21–28 caused no occurrence of powder dust, unlike bis(2-pyridinethiol-1-oxide) copper salt needle crystals. It was also found that the coated substance easily eluted out in the coating to again form needle crystals of bis(2-pyridinethiol-1-oxide) copper salt.

The coatings for the bottom of ship containing the coated bis(2-pyridinethiol-1-oxide) copper salts obtained in Examples 21–27 as an antifouling component in the proportion shown in Table 5, or the coated bis(2-pyridinethiol-1-oxide) copper salt obtained in Example 28 as an antifouling component in the proportion shown in Table 2 were prepared.

TABLE 5

Composition of ship bottom coatings 21–27

| Ingredient | parts by weight |
| --- | --- |
| Antifouling component (Examples 21–27) | 3 |
| Cuprous oxide | 20 |
| Iron oxide red | 8 |
| Talc | 5 |
| Resin | 10 |
| Rosin xylene solution | 25 |
| Amide wax | 2 |
| Xylene | 27 |
|  | 100 |

The rosin xylene solution, amide wax and resin shown in Table 5 are the same as those shown in Table 2.

When preparing the coatings for the bottom of ship, the coated bis(2-pyridinethiol-1-oxide) copper salts of Examples 21–28 did not scatter or cause irritation by inhalation, irritation to the skin or irritation to the mucous membrane, but showed strikingly improved workability. The properties of the prepared coatings were not adversely influenced, and coatings for the bottom of ship that were superior in long-term storage stability were obtained.

Effectiveness Test

The coatings for the bottom of ship that were obtained in Examples 21–28 were used in the above-mentioned effectiveness test. The results are shown in Table 6.

TABLE 6

Sea immersion test results (organisms adhesion area %)

| | Organisms adhesion area % | | | |
| --- | --- | --- | --- | --- |
| | 3 months | 6 months | 9 months | 12 months |
| Example 21 | 0 | 0 | 0 | 0 |
| Example 22 | 0 | 0 | 0 | 0 |
| Example 23 | 0 | 0 | 0 | 0 |
| Example 24 | 0 | 0 | 0 | 0 |
| Example 25 | 0 | 0 | 0 | 0 |
| Example 26 | 0 | 0 | 0 | 0 |
| Example 27 | 0 | 0 | 0 | 0 |
| Example 28 | 0 | 0 | 0 | 5 |

As is evident from Table 6, the coatings containing the antifouling components of Examples 21–28, which are for the bottom of ship, showed an antifouling effect over an extended period of time. It was also found that the effect was not inhibited at all by the covering with the compound of the present invention.

Industrial Applicability

The bis(2-pyridinethiol-1-oxide) copper salt of the present invention, which has been coated with one or more compounds selected from glycerin, dialkyl phthalate, lubricating oil, acrylic resin, rosin, fatty acid amide, dialkyl polysulfide, polybutene, paraffin and petrolatum, does not scatter, is easy to handle, and is superior in safety and workability. A coating for the bottom of a ship, which contains the bis(2-pyridinethiol-1-oxide) copper salt, does not exert any adverse influence on the storage stability or antifouling effect, and the effect of the salt does not change by the coating.

This application is based on patent application Nos. 11-072727 filed Mar. 17, 1999, 11-112957 filed Apr. 20, 1999 and 11-112958 filed Apr. 20, 1999 in Japan, the contents of which are hereby incorporated by reference.

What is claimed is:

1. A bis(2-pyridinethiol-1-oxide) copper salt coated with a compound consisting essentially of rosin.

2. The coated bis(2-pyridinethiol-1-oxide) copper salt of claim 1, wherein the rosin is coated in an amount of 1–40 parts by weight per 100 parts by weight of the bis(2-pyridinethiol-1-oxide) copper salt.

* * * * *